Figure 1:
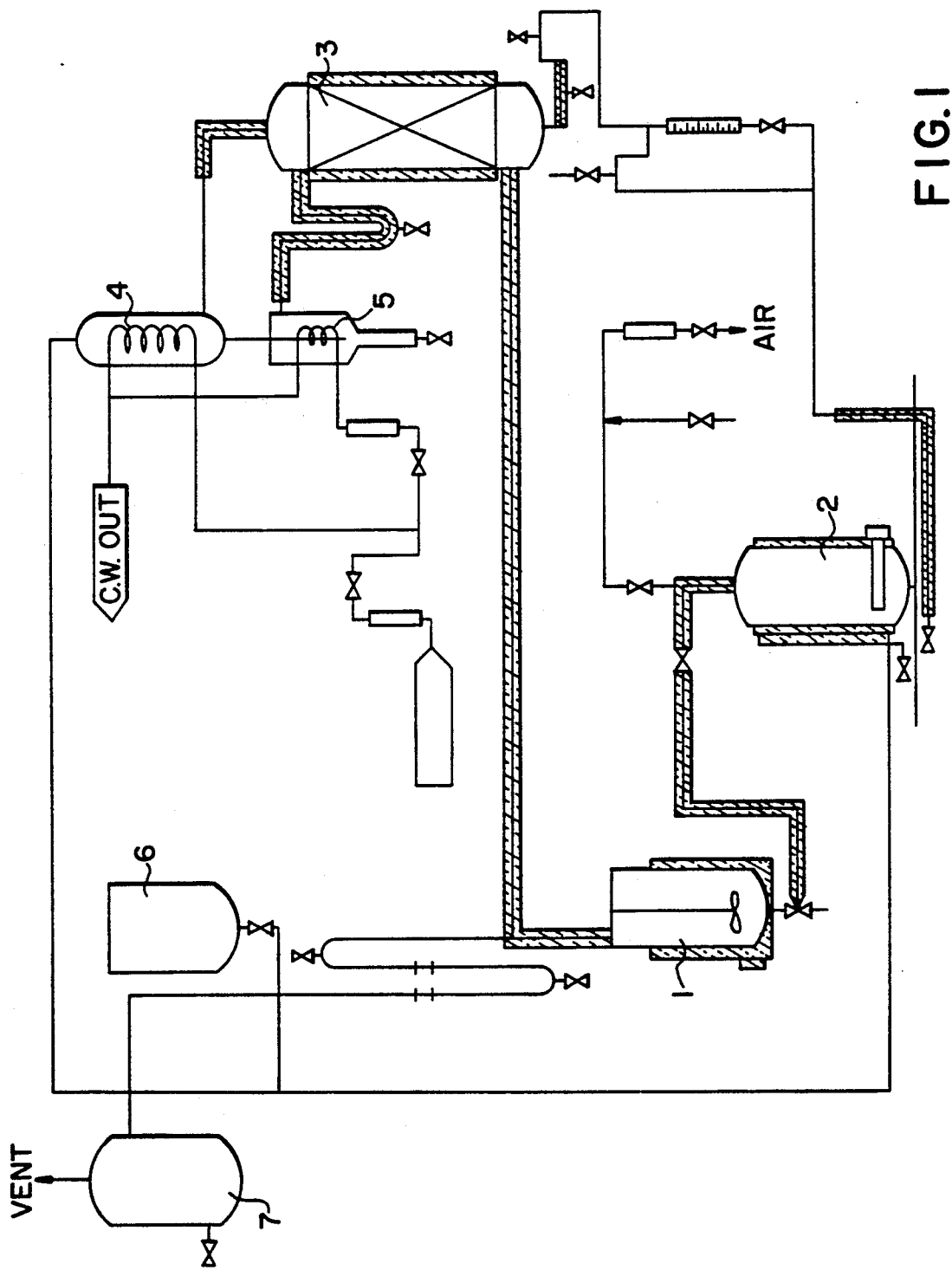

United States Patent [19]
Segall et al.

[11] Patent Number: 5,097,056

[45] Date of Patent: Mar. 17, 1992

[54] PROCESS FOR THE PREPARATION OF TRIARYL PHOSPHATES USING $H_3PO_4$ AND HARD CATION AS A CATALYST

[75] Inventors: Jeane Segall; Leonard M. Shorr, both of Haifa, Israel

[73] Assignee: Bromine Compounds Ltd., Beer-Sheva, Israel

[21] Appl. No.: 307,892

[22] Filed: Feb. 7, 1989

[30] Foreign Application Priority Data

Feb. 8, 1988 [IL] Israel ........................... 85349

[51] Int. Cl.$^5$ ............................................. C07F 9/02
[52] U.S. Cl. ................................. 558/110; 502/213
[58] Field of Search .............................. 558/110

[56] References Cited

U.S. PATENT DOCUMENTS 2,963,506 12/1960 Lewinski .................... 558/110

FOREIGN PATENT DOCUMENTS 178374  1/1966 U.S.S.R. ......................... 558/110
2215722 9/1989 United Kingdom ............ 558/110

OTHER PUBLICATIONS

"Phosphorous and Its Compounds", vol. 2, edited by John R. Wazer, Interscience publishers Ltd London (1961) pp. 1222, 1231, 1232.
"The Manufacture and Use of Selected Aryl and Alkylaryl Phosphate Esters", TASK 1, Feb. 1976, p. 19.
"The Chemistry and Uses of Fire Retardants", John W. Lyons, Wiley Interscience, pp. 41–45.

Primary Examiner—Mukund J. Shah
Assistant Examiner—Jyothsna Venkat
Attorney, Agent, or Firm—Michael N. Meller

[57] ABSTRACT

A process is described according to which triaryl phosphates are prepared by the reaction of one or more phenols with $H_3PO_4$, in the presence of a hard cation as a catalyst. Novel catalysts and catalyst precursors for this purpose are described.

6 Claims, 2 Drawing Sheets

FIG.I

PROCESS FOR THE PREPARATION OF TRIARYL PHOSPHATES USING H3PO4 AND HARD CATION AS A CATALYST

FIELD OF THE INVENTION

The present invention relates to a process for the manufacture of triaryl phosphates. More particularly, the invention relates to an improved process in which triaryl phosphate of high purity is obtained.

BACKGROUND OF THE INVENTION

According to the known art, triaryl phosphates are prepared by a process in which $POCl_3$ is reacted with the appropriate phenol at elevated temperatures in the presence of large amounts of $AlCl_3$ as a catalyst. Examples of triaryl phosphates to which the present invention is directed are tricresyl, triphenyl, phenylcresyl and phenyl-i-propylphenyl phosphates. Triaryl phosphates have a number of industrial applications, such as plasticizers for polymers, fire retardants, lubricant oil additives and hydraulic fluids.

The processes of the art, however, present several severe drawbacks. Firstly, HCl evolves as a waste product, and the process, among other common disadvantages of acid evolution, requires that glass-lined vessels be employed. Secondly, only relatively low conversions—of up to about 88%—are usually obtained. Thirdly, aromatic by-products are wasted and, together with the large amounts of catalyst employed, form wastes which are burdensome and must be disposed of, because of environmental hazards.

Replacing $POCl_3$ by $H_3PO_4$ potentially solves part of the above-mentioned problems, since the intermediates resulting from the reaction can be recycled, the corrosion problem is eliminated because $AlCl_3$ is not used, and no HCl evolves, and there is essentially no waste. This replacement, however, leads to impractically slow reactions which are not useful from an industrial point of view.

SUMMARY OF THE INVENTION

It has now been found, and this is an object of the invention, that it is possible to provide a process which employs $H_3PO_4$ and which can be carried out at attractive reaction rates.

It is therefore an object of the invention to provide a process for the preparation of triaryl phosphates from $H_3PO_4$ and the appropriate phenol or phenols, which permits to employ $H_3PO_4$, with all the advantages attached to it, and still provides industrially acceptable production rates and high purity.

The process for the preparation of triaryl phosphates according to the invention, in which a phenol or a mixture of two or more phenols is reacted with $H_3PO_4$, is characterized in that the reaction is catalyzed by the addition of a catalytically effective amount of an additive which liberates a hard cation when in soluted form. Preferably, the phenol is present in at least a small stiochiometric excess.

By "hard cation" is meant the group of cations so classified according to R. G. Pearson [J. Chem. Education, 45, pp. 581 and 643(1968)].

According to a preferred embodiment of the invention, the cation is selected from the group consisting essentially of: $B^{+++}$, $Cd^{++}$, $Sb^{+5}$, $Mg^{++}$, $Mn^{++}$, $Cu^{++}$, $Zn^{++}$, $Co^{++}$, $Li^+$, $Fe^{+++}$, $Al^{+++}$.

Examples of materials which liberate a hard cation when in soluted form are $H_3BO_3$, $CdSO_4.8H_2O$, $Sb_2O_5$, $Mg(OAc)_2.4H_2O$, $Mn(OAc)_2.4H_2O$, $CuSO_4.5H_2O$, $Zn(OAc)_2$, $CoSO_4.7H_2O$, $ZnSO_4.7H_2O$, $Li_2SO_4$, $Fe_2(SO_4)_3$, Mn dimethyl phosphate, Mg diallyl phosphate, Mg dimethyl phosphate, $MnSO_4$, $MgSO_4$, $Mg(OH)_2$, $Al(OH)_3$, $Al_2(SO_4)_3.18H_2O$. The amount of the said additive needed is generally less than 1-5 wt %.

According to a preferred embodiment of the invention, the process comprises the steps of:

a) continuously removing and separating the water produced in the reaction between $H_3PO_4$ and the phenol;

b) distilling the triaryl phosphate from the reaction mixture and recycling the intermediate and catalyst to the reaction mixture.

Preferably, the separation of the water is effected by means of an inert hydrocarbon, more preferably xylene. The injection of the latter into the system facilitates the removal of water from the vapors as well as its separation from the condensed distillate. It should be understood that efficient water separation is especially important for the promotion of the reaction. The inert hydrocarbon has the advantage of entraining water and thereby aiding to remove water and to obtain a greater degree of dryness. Efficient drying is important because the tertiary ester obtained in the reaction is easily hydrolizable, which leads to a deterioration of the product.

According to another preferred embodiment of the invention at least part of the phenol or phenolic mixture is fed to the reaction vessel in vapor form. The latent heat of phenolic vapors is exploited in this way, to meet part of the heat requirements of the reaction.

Also encompassed within the present invention is a catalyst for accelerating the reaction between a phenol and $H_3PO_4$, which catalyst comprises a material which in solution liberates a hard cation selected from the group consisting essentially of $H_3BO_3$, $CdSO_4.8H_2O$, $Sb_2O_5$, $Mg(OAc)_2.4H_2O$, $Mn(OAc)_2.4H_2O$, $CuSO_4.5H_2O$, $Zn(OAc)_2$, $CoSO_4.7H_2O$, $ZnSO_4.7H_2O$, $Li_2SO_4$, $Fe_2(SO_4)_3$, Mn dimethyl phosphate, Mg diallyl phosphate, Mg dimethyl phosphate, $MnSO_4$, $MgSO_4$, $Mg(OH)_2$, $Al(OH)_3$, $Al_2(SO_4)_3.18H_2O$.

The above and other characteristics and advantages of the invention will be better understood from the following illustrative and non-limitative examples.

GENERAL WORKUP PROCEDURE.

Phosphoric acid and an excess of the appropriate phenol or mixture of phenols were introduced into a flask. The mixture was heated with efficient stirring whereby a solution was obtained. As the reaction proceeded the water formed was removed by distillation with phenolic vapors through a Dean-Stark trap which contained xylene for easier water separation. Some xylene returned to the column, but large amounts in the reactor were avoided so as to maintain high reaction temperatures. The dry phenol was continuously recycled into the reaction mixture. Samples of the reaction product were withdrawn intermittently and analyzed by paper chromatography coupled with U.V. spectroscopy. In one instance the reaction product was distilled under reduced pressure and the distillate, consisting of unreacted phenol and TPP was analyzed and identified by G.C. in comparison with samples of the pure compounds. In another instance the reaction product was mixed with a ten-fold excess of water, whereby Triphenyl Phosphate precipitated. After further washing with water and after drying, an almost colorless product was obtained which was found by G.C. to be over 99% pure.

EXAMPLE 1

A series of reaction experiments was carried out, according to the general procedure described above, to test the influence of different additives which liberate hard cations on the reaction rate. The phenol employed was cresol and the ester formed in the reaction was tricresyl phosphate (TCP). In all cases 0.6 wt %, relative to the cresol, of the additive was employed, and was added gradually in three equal portions. The reaction mixture was assayed after six hours of reaction, to determine TCP concentration. The results of these experiments are set forth in Table I below, which also shows results obtained in the absence of an additive, as well as with additives comprising non-hard ions, viz., $Sb_2O_3$, $HgSO_4$, $Ag_2SO_4$, Zr oxalate, for comparison purposes.

EXAMPLE 2

39.2 g (0.4 mole) of 100% $H_3PO_4$ were placed in a 250 ml flask, and 177 g (1.3 moles) of o-isopropylphenol and 0.8 g Mg dimethyl phosphate catalyst were added. A 40 cm long column (d=5 cm) filled with Raschig rings was attached to the flask which was mechanically stirred. On top of the column there was placed a Dean-Stark trap filled with xylene and a condenser.

The reaction product after 5.5 hours contained (on a molar basis):

43.2% tri-isopropylphenyl phosphate;

56.8% di-isopropylphenyl phosphate, the rest being the free phenol. The product was free both of $H_3PO_4$ and of the mono-isopropylphenyl phosphoric acid.

EXAMPLE 3

To a standard reaction set-up there were added 1.6 moles of 100% $H_3PO_4$, 4.9 moles of freshly distilled (m+p)-cresol, 3.2 g of Mn dimethyl phosphate catalyst and 0.7 g of the oxidation inhibitor 2,6-di-tert-butyl-α-methoxy-p-cresol (ex Ethyl Corp.). The reaction was performed under a $N_2$ blanket in order to avoid oxidation and discoloration of the cresol.

When the reaction yielded 2.7 moles of $H_2O$ (according to $H_2O$ collected) it was stopped and the product flashed out at 3-10 mmHg and a maximum pot temperature of 280° C. The time required for this flash distillation was 1.75 hours. The distillate obtained, 518 g, contained: 44% cresol and 56% TCP in addition to very small amounts of the oxidation inhibitor and xylene. The cold trap consisted of a very small amount (~1 g) of $H_2O$ and xylene.

EXAMPLE 4

This example illustrates the continuous production of TCP, using vaporized cresol. The apparatus used is shown in FIG. 1. The reactor is shown by numeral 1, and consists of a 20 l reactor made of 316 stainless steel and fitted with a turbine stirrer, thermowell and electric heater. Cresol is fed to the reactor 1 from the cresol boiler 2, which consists of a 10 lit., 316 SS vessel, with electric heater which, when heated, causes cresol vapors to flow into reactor 1. The separation column 3 has a diameter of 4 inches and a height of 100 cm, and is filled with 6×6 mm glass Raschig rings. Numeral 4 indicates a standard condenser and numeral 5 a standard water separator. Numeral 6 is the cresol tank and numeral 7 the overflow tank. The top of the reactor is connected to the distillation column and the $H_2O$ separator which contains xylene.

Several TCP production runs were carried out in the system of FIG. 1. In all the runs 6 l of cresol were placed in the boiler and 6 l of cresol in the reactor. The cresol was refluxed and dried azeotropically prior to the introduction of the $H_3PO_4$. 820 ml of 92.4% $H_3PO_4$ (13.72 moles) were fed into the hot reactor during about 10 minutes, while cresol vapors were circulated in the system. Water resulting from both the initial $H_3PO_4$ and from the reaction distilled off and was collected in the xylene separator. The results of a representative run (Run 5) are shown in Table II below.

Figure 2:
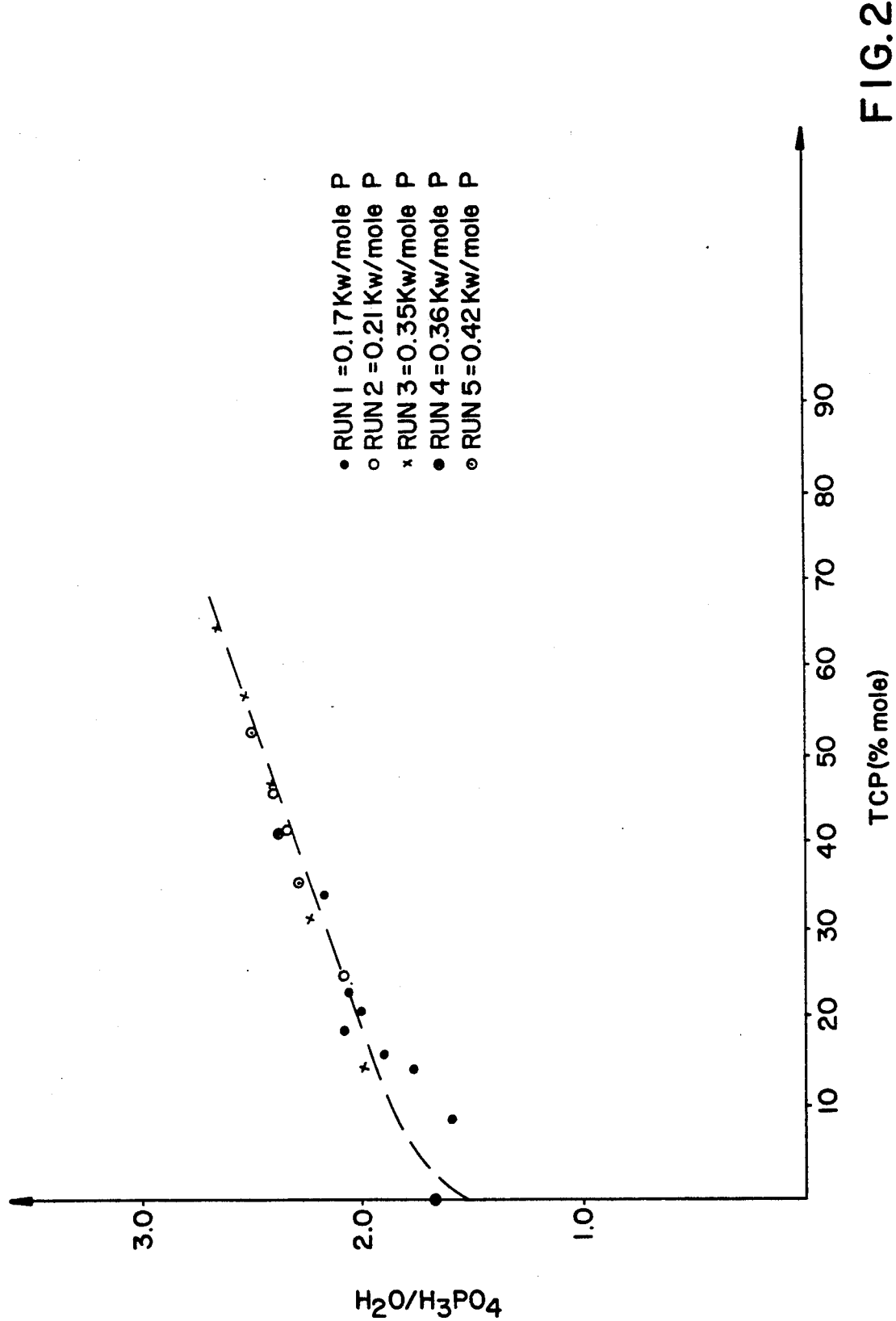

FIG. 2 shows the rate of formation of TCP at various heat inputs as a function of M (the molar ratio $H_2O/H_3PO_4$), for the above and additional four runs. The results shown in FIG. 2 are self-explicative.

The above examples and description have been given for the purpose of illustrations and are not intended to be limitative. Many variations can be effected in the process of the invention, without exceeding its scope.

TABLE I

Influence of Additives on the Rate of TCP formation
TCP Formed After Six Hours (mole %)

| Additive | TCP formed (mole %) |
| --- | --- |
| None | 43 |
| $Sb_2O_3$ | 40 |
| $HgSO_4$ | 47 |
| $Ag_2SO_4$ | 43 |
| Zr oxalate | 48 |
| $H_3BO_3$ | 60 |
| $CdSO_4.8H_2O$ | 65 |
| $Sb_2O_5$ | 71 |
| $Mg(OAc)_2.4H_2O$ | 68 |
| $Mn(OAc)_2.4H_2O$ | 68 |
| $CuSO_4.5H_2O$ | 71 |
| $Zn(OAc)_2$ | 72 |
| $CoSO_4.7H_2O$ | 74 |
| $ZnSO_4.7H_2O$ | 78 |
| $Li_2SO_4$ | 78 |
| $Fe_2(SO_4)_3$ | 78 |
| Mn dimethyl phosphate | 78 |
| Mg diallyl phosphate | 78 |
| Mg dimethyl phosphate | 80 |
| $MnSO_4$ | 82 |
| $MgSO_4$ | 82 |
| $Mg(OH)_2$ | 82 |
| $Al(OH)_3$ | 82 |
| $Al_2(SO_4)_3.18H_2O$ | 85 |

TABLE II

| | | Experimental Results for Run No. 5 | | | | | | |
| --- | --- | --- | --- | --- | --- | --- | --- | --- |
| Time | mole $H_2O$/ | Product Analysis (% w/w) | | | | | Temperature (°C.) | |
| (hrs) | mole P | $H_3PO_4$ | MCP | DCP | TCP | Cresol | Pot | Head |
| 3 | 1.60 | 0.7 | 4 | 36 | 19 | 41 | 240 | 203 |
| 4 | 1.72 | 0.4 | 3 | 30 | 27 | 34 | 255 | 204 |
| 5.25 | 1.92 | 0.3 | 4 | 37 | 31 | 32 | 249 | 204 |

TABLE II-continued

| | | Experimental Results for Run No. 5 | | | | | | |
|---|---|---|---|---|---|---|---|---|
| Time | mole H$_2$O/ | Product Analysis (% w/w) | | | | | Temperature (°C.) | |
| (hrs) | mole P | H$_3$PO$_4$ | MCP | DCP | TCP | Cresol | Pot | Head |
| 5.75 | 2.00 | 0.2 | 2 | 25 | 43 | 33 | 243 | 203 |

MCP = monocresyl phosphate
DCP = dicresyl phosphate
TCP = tricresyl phosphate

We claim:

1. A process for the preparation of triaryl phosphates, in which a phenol or a mixture of two or more phenols is reacted with H$_3$PO$_4$, which comprises
   a) catalyzing the reaction by the addition of a catalytically effective amount of an additive which liberates a hard cation when in soluted form;
   b) continuously removing and separating the water produced in the reaction between H$_3$PO$_4$ and the phenol; and
   c) distilling the triaryl phosphate from the reaction mixture and recycling the intermediate and catalyst to the reaction mixture.

2. A process according to claim 1, wherein the cation is selected from the group consisting essentially of: B$^{+++}$, Cd$^{++}$, Sb$^{+5}$, Mg$^{++}$, Mn$^{++}$, Cu$^{++}$, Zn$^{++}$, Co$^{++}$, Li$^+$, Fe$^{+++}$, Al$^{+++}$.

3. A process according to claim 2, wherein the additive is selected from the group consisting essentially of H$_3$BO$_3$, CdSO$_4$.8H$_2$O, Sb$_2$O$_5$, Mg(OAc)$_2$.4H$_2$O, Mn(OAc)$_2$.4H$_2$O, CuSO$_4$.5H$_2$O, Zn(OAc)$_2$, CoSO$_4$.7H$_2$O, ZnSO$_4$.7H$_2$O, Li$_2$SO$_4$, Fe$_2$(SO$_4$)$_3$, Mn dimethyl phosphate, Mg diallyl phosphate, Mg dimethyl phosphate, MnSO$_4$, MgSO$_4$, Mg(OH)$_2$, Al(OH)$_3$, Al$_2$(SO$_4$)$_3$.18H$_2$O.

4. A process according to claim 1, wherein separation of the water is effected by means of an inert hydrocarbon.

5. A process according to claim 4, wherein the inert hydrocarbon is xylene.

6. A process according to claim 1, wherein at least part of the phenol or phenolic mixture is fed to the reaction vessel in vapor form.

* * * * *